(12) United States Patent
Mohammadi

(10) Patent No.: US 8,029,645 B2
(45) Date of Patent: Oct. 4, 2011

(54) SOFT AND STRONG FIBROUS STRUCTURES AND METHODS FOR MAKING SAME

(75) Inventor: Khosrow Parviz Mohammadi, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/987,330

(22) Filed: Jan. 10, 2011

(65) Prior Publication Data
US 2011/0168342 A1 Jul. 14, 2011

Related U.S. Application Data

(60) Provisional application No. 61/294,909, filed on Jan. 14, 2010.

(51) Int. Cl.
*D21H 11/12* (2006.01)
(52) U.S. Cl. ............ 162/129; 162/91; 162/99; 162/111; 162/112; 162/130; 162/141; 162/142; 162/148; 162/149
(58) Field of Classification Search ............... 162/91, 162/99, 111, 112, 129, 130, 141, 142, 148, 162/149; 428/152, 153, 154, 219, 221, 292.7, 428/311.91, 340, 342, 357, 364, 369, 401
See application file for complete search history.

(56) References Cited

U.S. PATENT DOCUMENTS

| | | | |
|---|---|---|---|
| 2,663,907 A | 12/1953 | Downing et al. |
| 2,729,560 A | 1/1956 | House et al. |
| 3,079,127 A | 7/1963 | Ostmann, Jr. |
| 3,301,746 A | 1/1967 | Sanford et al. |
| 3,353,682 A | 11/1967 | Pall et al. |
| 3,382,140 A | 5/1968 | Henderson et al. |
| 3,723,231 A | 3/1973 | Clay et al. |
| 3,794,558 A | 2/1974 | Back et al. |
| 3,825,381 A | 7/1974 | Dunning et al. |
| 3,949,035 A | 4/1976 | Dunning et al. |
| 3,974,025 A | 8/1976 | Ayers |
| 3,994,771 A | 11/1976 | Morgan, Jr. et al. |
| 4,087,316 A | 5/1978 | Jividen et al. |
| 4,100,324 A | 7/1978 | Anderson et al. |
| 4,191,609 A | 3/1980 | Trokhan |
| 4,257,842 A | 3/1981 | Ciaccia et al. |
| 4,261,139 A | 4/1981 | Pogue |
| 4,300,981 A | 11/1981 | Carstens |
| 4,637,859 A | 1/1987 | Trokhan |
| H1672 H | 8/1997 | Hermans et al. |
| 5,856,006 A | 1/1999 | Asai et al. |
| 6,068,732 A | 5/2000 | Cassidy et al. |
| 6,163,943 A | 12/2000 | Johansson et al. |
| 7,691,472 B2 | 4/2010 | Vinson et al. |
| 7,811,613 B2 | 10/2010 | Vinson et al. |
| 2003/0000666 A1 | 1/2003 | Mansson et al. |
| 2003/0093051 A1 | 5/2003 | Malowaniec et al. |
| 2004/0084167 A1 | 5/2004 | Vinson et al. |
| 2004/0154763 A1 * | 8/2004 | Polat et al. .................... 162/129 |
| 2004/0231810 A1 | 11/2004 | Rousu et al. |
| 2005/0091811 A1 | 5/2005 | Billgren et al. |
| 2005/0238699 A1 | 10/2005 | Kleinwaechter |
| 2006/0108082 A1 | 5/2006 | Bogdanski et al. |
| 2006/0288639 A1 | 12/2006 | Vinson et al. |
| 2007/0011762 A1 | 1/2007 | Vinson et al. |
| 2007/0107863 A1 | 5/2007 | Edwards et al. |
| 2008/0003435 A1 | 1/2008 | Trueman et al. |
| 2009/0054858 A1 * | 2/2009 | Cheng et al. .................. 604/358 |

FOREIGN PATENT DOCUMENTS

| | | |
|---|---|---|
| EP | 1 548 165 A1 | 6/2005 |
| WO | WO 96/12849 A1 | 5/1996 |
| WO | WO 00/59439 A1 | 10/2000 |
| WO | WO 00/78127 A1 | 12/2000 |
| WO | WO 01/52911 A2 | 7/2001 |
| WO | WO 03/000990 A1 | 1/2003 |
| WO | WO 2006/137041 A2 | 12/2006 |
| WO | WO 2007/091216 | 8/2007 |
| WO | WO 2008/010187 A2 | 1/2008 |

OTHER PUBLICATIONS

Potikha, et al. "A Mutant of *Arabidopsis thaliana* Displaying Altered Patterns of Cellulose Deposition", *Plant Journal*, vol. 7, No. 3, pp. 453-460 (No. 3.).
Zhang, et al., "A Simple and Efficient Method for Isolating Trichomes for Downstream Analyses", *Plant and Cell Physiology*, vol. 45, No. 2, pp. 221-224 (Feb. 2004) XPOO2409939.
Kim, et al., "Cotton Fiber Growth In Planta and In Vitro, Models for Plant Cell Elongation and Cell Wall Biogenesis", *Plant Physiology*, vol. 127, pp. 1361-66 (2001).
"The New Royal Horticultural Society Dictionary of Gardening", vol. 4, p. 359 (1992).
Compton. "Upper North Wakashan and Southern Timishian Ethnobotany: The Knowledge and Usage of Plants and Fungi Among the Oweekeno, Hanaksiala (Kitlope and Kemano), Haisla (Kitamaat) and Kitasoo Peoples of the Central and North Coasts of British Columbia", *The University of British Columbia, Ph.D. Thesis*, p. 256 (1993).
Kuhlein, et al., WSDOT-Ethnobotany-Herbs [Online] 1991-1994 XP002406397; retrieved from the Internet; URL:http://www.wsdot.wa.gov/Environment/CulRes/herbs.htm#Typha (retrieved on Nov. 9, 2006) Abstract.

(Continued)

*Primary Examiner* — Eric Hug
*Assistant Examiner* — Peter Chin
(74) *Attorney, Agent, or Firm* — Christian M. Best; C. Brant Cook

(57) ABSTRACT

Soft and strong fibrous structures and more particularly soft and strong fibrous structures that contains less softwood fibers than known fibrous structures and methods for making such soft and strong fibrous structures are provided.

33 Claims, 6 Drawing Sheets

OTHER PUBLICATIONS

Tan: "Cattails (*Typha augustifolia*")" [Online] 2001, XP002406398; retrieved from the Internet: URL:http:/www.naturia.per.sg/buloh/plants/cattail.htm (retreived on Nov. 9, 2006) Whole documents, specialty uses.
Riley, et al., "The Mbeere in Kenya", vol. II, Botanical Identities and Uses, pp. 50-51 and 102-103 (1988).
Definition of trichome [online], [retrieved on Apr. 14, 2009], Retrieved from the Internet www.yourdictionary.com/trichome, one page.
International Search Report and Written Opinion (PCT WO 2006/137041).
International Search Report and Written Opinion (PCT WO 2006/137040).
International Search Report and Written Opinion (PCT WO 2009/024897).
U.S. Appl. No. 11/436,494 Office Action dated Nov. 6, 2008.
U.S. Appl. No. 11/436,494 Office Action dated Apr. 30, 2009.
U.S. Appl. No. 11/436,494 Office Action dated May 20, 2009.
U.S. Appl. No. 11/436,494 Office Action dated Jul. 2, 2009.
U.S. Appl. No. 11/436,494 Office Action dated Dec. 1, 2009.
U.S. Appl. No. 11/436,494 Office Action dated Jan. 13, 2010.
U.S. Appl. No. 11/436,494 Office Action dated Jun. 24, 2010.
U.S. Appl. No. 11/436,501 Office Action dated Aug. 1, 2008.
U.S. Appl. No. 11/436,501 Office Action dated Jan. 9, 2009.
U.S. Appl. No. 11/436,501 Office Action dated May 13, 2009.
U.S. Appl. No. 11/436,501 Office Action dated Jul. 22, 2009.
U.S. Appl. No. 11/436,501 Office Action dated Dec. 24, 2009.
U.S. Appl. No. 11/436,501 Office Action dated Jan. 26, 2010.
U.S. Appl. No. 11/894,519 Office Action dated Mar. 31, 2010.
U.S. Appl. No. 11/894,519 Office Action dated Sep. 14, 2010.
U.S. Appl. No. 11/894,519 Office Action dated Mar. 25, 2011.
International Search Report and Written Opinion (International Application No. PCT/US2011/020648).
All Office Actions for U.S. Appl. No. 11/436,494.
All Office Actions for U.S. Appl. No. 12/851,923.
All Office Actions for U.S. Appl. No. 11/436,501.
All Office Actions for U.S. Appl. No. 11/894,519.

* cited by examiner

SOFT AND STRONG FIBROUS STRUCTURES AND METHODS FOR MAKING SAME

CROSS REFERENCE TO RELATED APPLICATION

This application claims the benefit of U.S. Provisional Application No. 61/294,909, filed Jan. 14, 2010, which is hereby incorporated by reference in its entirety.

FIELD OF THE INVENTION

The present invention relates to soft and strong fibrous structures and more particularly to soft and strong fibrous structures that comprise less softwood fibers than known fibrous structures and methods for making such soft and strong fibrous structures.

BACKGROUND OF THE INVENTION

Historically, fibrous structures, such as fibrous structures that are used to make sanitary tissue products, have been made with softwood fibers and hardwood fibers. For example, softwood fibers have typically made up greater than 20% by weight on a dry fiber basis of through-air-dried fibrous structures. The softwood fibers are longer fibers than the hardwood fibers and they provide greater strength properties to the fibrous structures than do the hardwood fibers. However, softwood fibers negatively impact the softness of the fibrous structures.

Formulators have for years attempted to balance the level of softwood fibers in their fibrous structures to ensure adequate strength of the fibrous structures while at the same time trying to minimize the level of softwood fibers to avoid negatively impacting the softness of the fibrous structures. The problem has been that formulators have been unable to reliably make fibrous structures, especially through-air-dried ("TAD") fibrous structures that are used to make sanitary tissue products that contain less than 20% by weight of softwood fibers on a dry fiber basis of the fibrous structure, due to lower resulting strength in the fibrous structures which can lead to product quality issues and/or sheet breaks during processing. If formulators use less than 20% by weight on a dry fiber basis of softwood fibers to make fibrous structures and/or sanitary tissue products, the softwood fibers would need to have excessive refining and/or chemical strength agents to achieve the desired level of strength needed for product quality and/or reliability (avoid sheet breaks during making and/or processing). Both of these actions negatively impact softness of the fibrous structure and/or sanitary tissue product.

Accordingly, there is a need for a fibrous structure that comprises less softwood fibers, for example a 5% or more by weight reduction on a dry fiber basis, than traditional fibrous structures, especially traditional through-air-dried fibrous structures, without negatively impacting the strength of the resulting fibrous structures and reducing machine reliability, sanitary tissue products comprising same and methods for making same.

SUMMARY OF THE INVENTION

The present invention fulfills the need described above by providing a fibrous structure that comprises less softwood fibers, for example a 5% or more by weight reduction on a dry fiber basis, than traditional fibrous structures, especially traditional through-air-dried fibrous structures, without negatively impacting the strength and/or softness of the fibrous structures and optionally, positively impacting the softness of the fibrous structures, sanitary tissue products comprising such fibrous structures and methods for making such fibrous structures.

In one example of the present invention, a fibrous structure, for example a through-air-dried fibrous structure, exhibiting a basis weight of from about 10 to about 120 g/m$^2$, wherein the fibrous structure comprises greater than 50% by weight on a dry fiber basis of pulp fibers, wherein greater than 0% but less than 20% by weight on a dry fiber basis of the pulp fibers are softwood fibers, is provided.

In another example of the present invention, a single- or multi-ply sanitary tissue product comprising one or more fibrous structures of the present invention, is provided.

In yet another example of the present invention, a sanitary tissue product, for example a sanitary tissue product comprising a through-air-dried fibrous structure, comprising greater than 50% by weight on a dry fiber basis of pulp fibers, wherein less than 20% by weight on a dry fiber basis of the pulp fibers are softwood fibers, optionally, wherein the sanitary tissue product comprises trichome fibers, and wherein the sanitary tissue product exhibits a total dry tensile of at least 300 g/in as measured according to the Total Dry Tensile Test Method described herein, is provided.

In even another example of the present invention, a fibrous structure, for example a through-air-dried fibrous structure, comprising a plurality of pulp fibers, wherein greater than 0% but less than 20% by weight on a dry fiber basis of the pulp fibers are softwood fibers and wherein the fibrous structure comprises fibers derived from a fiber-producing source that has a growing cycle of less than 800 and/or less than 400 and/or less than 200 and/or less than 100 days. By using fibers derived from fiber-producing sources that have a growing cycle of less than 800 and/or less than 400 and/or less than 200 and/or less than 100 days, these fibrous structures are significantly more sustainable than fibrous structures that do not use such fibers.

In still another example of the present invention, a fibrous structure, for example a through-air-dried fibrous structure, comprising a plurality of fibers and being void of surface softening agents, such as quaternary ammonium surface softening agents and silicones, wherein the fibrous structure exhibits a Slip-and-Stick Coefficient of Friction of less than 0.8 and/or less than 0.75 and/or less than 0.7 as measured according to the Slip-and-Stick Coefficient of Friction Test Method as described herein.

In yet another example of the present invention, a fibrous structure, for example a through-air-dried fibrous structure, comprising individualized trichomes and greater than 0% but less than 20% by weight on a dry fiber basis of softwood fibers and wherein the fibrous structure exhibits a Slip-and-Stick Coefficient of Friction as measured according to Slip-and-Stick Coefficient of Friction Test Method of less than 20% compared to the same fibrous structure void of the individualized trichomes, is provided.

In even still another example of the present invention, a fibrous structure, for example a through-air-dried fibrous structure, comprising fibers, wherein the weight ratio of softwood fibers to non-softwood fibers within the fibrous structure is less than 1:4 and/or less than 1:5 and/or less than 1:6 and/or less than 1:7 and/or less than 1:8 and/or less than 1:9, is provided.

Accordingly, the present invention provides fibrous structures that comprise less softwood fibers than previously known, sanitary tissue products comprising such fibrous structures and methods for making such fibrous structures.

DETAILED DESCRIPTION OF THE INVENTION

Definitions

Figure 1:
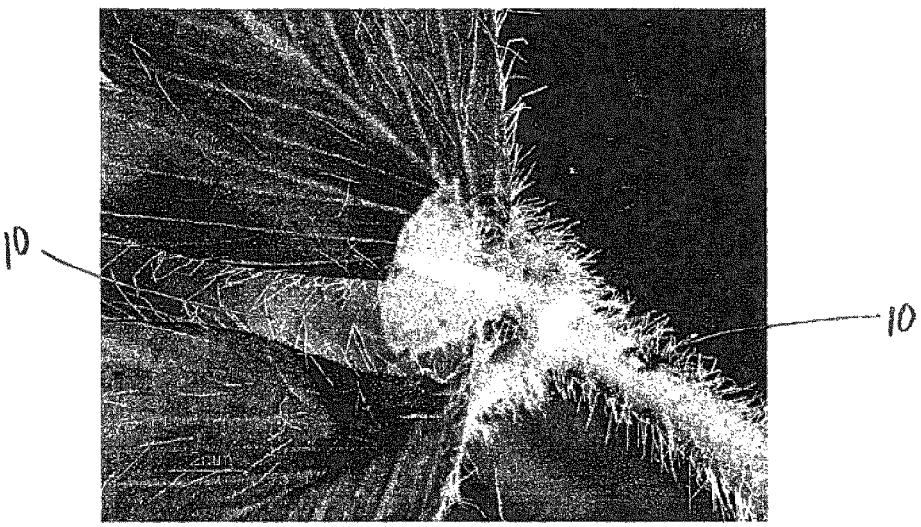
FIG. 1 is a light micrograph of a leaf and leaf stem illustrating trichomes present on red clover, *Trifolium pratense* L.

"Trichome" as used herein means an epidermal attachment of a varying shape, structure and/or function of a non-seed portion of a plant. In one example, a trichome is an outgrowth of the epidermis of a non-seed portion of a plant. The outgrowth may extend from an epidermal cell. In one embodiment, the outgrowth is a trichome fiber. The outgrowth may be a hairlike or bristlelike outgrowth from the epidermis of a plant.

Trichomes may protect the plant tissues present on a plant. Trichomes may for example protect leaves and stems from attack by other organisms, particularly insects or other foraging animals and/or they may regulate light and/or temperature and/or moisture. They may also produce glands in the forms of scales, different papills and, in roots, often they may function to absorb water and/or moisture.

A trichome may be formed by one cell or many cells.

The term "individualized trichome" as used herein means trichomes which have been artificially separated by a suitable method for individualizing trichomes from their host plant. In other words, individualized trichomes as used herein means that the trichomes become separated from a non-seed portion of a host plant by some non-naturally occurring action. In one example, individualized trichomes are artificially separated in a location that is sheltered from nature. Primarily, individualized trichomes will be fragments or entire trichomes with essentially no remnant of the host plant attached. However, individualized trichomes can also comprise a minor fraction of trichomes retaining a portion of the host plant still attached, as well as a minor fraction of trichomes in the form of a plurality of trichomes bound by their individual attachment to a common remnant of the host plant. Individualized trichomes may comprise a portion of a pulp or mass further comprising other materials. Other materials includes non-trichome-bearing fragments of the host plant.

In one example of the present invention, the individualized trichomes may be classified to enrich the individualized trichomal content at the expense of mass not constituting individualized trichomes.

Individualized trichomes may be converted into chemical derivatives including but not limited to cellulose derivatives, for example, regenerated cellulose such as rayon; cellulose ethers such as methyl cellulose, carboxymethyl cellulose, and hydroxyethyl cellulose; cellulose esters such as cellulose acetate and cellulose butyrate; and nitrocellulose. Individualized trichomes may also be used in their physical form, usually fibrous, and herein referred to "trichome fibers", as a component of fibrous structures.

Trichome fibers are different from seed hair fibers in that they are not attached to seed portions of a plant. For example, trichome fibers, unlike seed hair fibers, are not attached to a seed or a seed pod epidermis. Cotton, kapok, milkweed, and coconut coir are non-limiting examples of seed hair fibers.

Further, trichome fibers are different from nonwood bast and/or core fibers in that they are not attached to the bast, also known as phloem, or the core, also known as xylem portions of a nonwood dicotyledonous plant stem. Non-limiting examples of plants which have been used to yield nonwood bast fibers and/or nonwood core fibers include kenaf, jute, flax, ramie and hemp.

Further trichome fibers are different from monocotyledonous plant derived fibers such as those derived from cereal straws (wheat, rye, barley, oat, etc), stalks (corn, cotton, sorghum, *Hesperaloe funifera*, etc.), canes (bamboo, bagasse, etc.), grasses (esparto, lemon, sabai, switchgrass, etc), since such monocotyledonous plant derived fibers are not attached to an epidermis of a plant.

Further, trichome fibers are different from leaf fibers in that they do not originate from within the leaf structure. Sisal and abaca are sometimes liberated as leaf fibers.

Finally, trichome fibers are different from wood pulp fibers since wood pulp fibers are not outgrowths from the epidermis of a plant; namely, a tree. Wood pulp fibers rather originate from the secondary xylem portion of the tree stem.

"Fiber" as used herein means an elongate physical structure having an apparent length greatly exceeding its apparent diameter, i.e. a length to diameter ratio of at least about 10. Fibers having a non-circular cross-section and/or tubular shape are common; the "diameter" in this case may be considered to be the diameter of a circle having cross-sectional area equal to the cross-sectional area of the fiber. More specifically, as used herein, "fiber" refers to fibrous structure-making fibers. The present invention contemplates the use of a variety of fibrous structure-making fibers, such as, for example, natural fibers, such as trichome fibers and/or wood pulp fibers, or synthetic fibers, or any other suitable fibers, and any combination thereof.

Natural fibrous structure-making fibers useful in the present invention include animal fibers, mineral fibers, other plant fibers (in addition to the trichomes of the present invention) and mixtures thereof. Animal fibers may, for example, be selected from the group consisting of: wool, silk and mixtures thereof. The other plant fibers may, for example, be derived from a plant selected from the group consisting of: wood, cotton, cotton linters, flax, sisal, abaca, hemp, *hesperaloe*, jute, bamboo, bagasse, kudzu, corn, *sorghum*, gourd, agave, loofah and mixtures thereof.

Wood fibers; often referred to as wood pulps include chemical pulps, such as kraft (sulfate) and sulfite pulps, as well as mechanical and semi-chemical pulps including, for example, groundwood, thermomechanical pulp, chemi-mechanical pulp (CMP), chemi-thermomechanical pulp (CTMP), neutral semi-chemical sulfite pulp (NSCS). Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified and/or layered web. U.S. Pat. Nos. 4,300,981 and 3,994,771 are incorporated herein by reference for the purpose of disclosing layering of hardwood and softwood fibers. Also applicable to the present invention are fibers derived from recycled paper, which may contain any or all of the above categories as well as other non-fibrous materials such as fillers and adhesives used to facilitate the original papermaking.

The wood pulp fibers may be short (typical of hardwood fibers) or long (typical of softwood fibers). Non-limiting examples of short fibers include fibers derived from a fiber source selected from the group consisting of Acacia, Eucalyptus, Maple, Oak, Aspen, Birch, Cottonwood, Alder, Ash, Cherry, Elm, Hickory, Poplar, Gum, Walnut, Locust, Sycamore, Beech, Catalpa, Sassafras, Gmelina, Albizia, Anthocephalus, and Magnolia. Non-limiting examples of long fibers include fibers derived from Pine, Spruce, Fir, Tamarack, Hemlock, Cypress, and Cedar. Softwood fibers derived from the kraft process and originating from more-northern climates may be preferred. These are often referred to as northern softwood kraft (NSK) pulps.

Synthetic fibers may be selected from the group consisting of: wet spun fibers, dry spun fibers, melt spun (including melt blown) fibers, synthetic pulp fibers and mixtures thereof. Synthetic fibers may, for example, be comprised of cellulose (often referred to as "rayon"); cellulose derivatives such as esters, ether, or nitrous derivatives; polyolefins (including polyethylene and polypropylene); polyesters (including polyethylene terephthalate); polyamides (often referred to as "nylon"); acrylics; non-cellulosic polymeric carbohydrates (such as starch, chitin and chitin derivatives such as chitosan); polylactic acids, polyhydroxyalkanoates, polycaprolactones, and mixtures thereof. In one example, synthetic fibers may be used as binding agents.

The web (fibrous structure) of the present invention may comprise fibers, films and/or foams that comprises a hydroxyl polymer and optionally a crosslinking system. Non-limiting examples of suitable hydroxyl polymers include polyols, such as polyvinyl alcohol, polyvinyl alcohol derivatives, polyvinyl alcohol copolymers, starch, starch derivatives, chitosan, chitosan derivatives, cellulose derivatives such as cellulose ether and ester derivatives, gums, arabinans, galactans, proteins and various other polysaccharides and mixtures thereof. For example, a web of the present invention may comprise a continuous or substantially continuous fiber comprising a starch hydroxyl polymer and a polyvinyl alcohol hydroxyl polymer produced by dry spinning and/or solvent spinning (both unlike wet spinning into a coagulating bath) a composition comprising the starch hydroxyl polymer and the polyvinyl alcohol hydroxyl polymer.

"Fiber Length", "Average Fiber Length" and "Weighted Average Fiber Length", are terms used interchangeably herein all intended to represent the "Length Weighted Average Fiber Length" as determined for example by means of a Kajaani FiberLab Fiber Analyzer commercially available from Metso Automation, Kajaani Finland. The instructions supplied with the unit detail the formula used to arrive at this average. The recommended method for measuring fiber length using this instrument is essentially the same as detailed by the manufacturer of the FiberLab in its operation manual. The recommended consistencies for charging to the FiberLab are somewhat lower than recommended by the manufacturer since this gives more reliable operation. Short fiber furnishes, as defined herein, should be diluted to 0.02-0.04% prior to charging to the instrument. Long fiber furnishes, as defined herein, should be diluted to 0.15%-0.30%. Alternatively, fiber length may be determined by sending the short fibers to a contract lab, such as Integrated Paper Services, Appleton, Wis.

Fibrous structures may be comprised of a combination of long fibers and short fibers.

Non-limiting examples of suitable long fibers for use in the present invention include fibers that exhibit an average fiber length of less than about 7 mm and/or less than about 5 mm and/or less than about 3 mm and/or less than about 2.5 mm and/or from about 1 mm to about 5 mm and/or from about 1.5 mm to about 3 mm and/or from about 1.8 mm to about 4 mm and/or from about 2 mm to about 3 mm.

Non-limiting examples of suitable short fibers suitable for use in the present invention include fibers that exhibit an average fiber length of less than about 5 mm and/or less than about 3 mm and/or less than about 1.2 mm and/or less than about 1.0 mm and/or from about 0.4 mm to about 5 mm and/or from about 0.5 mm to about 3 mm and/or from about 0.5 mm to about 1.2 mm and/or from about 0.6 mm to about 1.0 mm.

The individualizes trichomes used in the present invention may include trichome fibers. The trichome fibers may be characterized as either long fibers or short fibers.

"Fibrous structure" as used herein means a structure that comprises one or more fibers. Non-limiting examples of processes for making fibrous structures include known wet-laid papermaking processes and air-laid papermaking processes. Such processes typically include steps of preparing a fiber composition in the form of a suspension in a medium, either wet, more specifically aqueous medium, or dry, more specifically gaseous, i.e. with air as medium. The aqueous medium used for wet-laid processes is oftentimes referred to as a fiber slurry. The fibrous suspension is then used to deposit a plurality of fibers onto a forming wire or belt such that an embryonic fibrous structure is formed, after which drying and/or bonding the fibers together results in a fibrous structure. Further processing the fibrous structure may be carried out such that a finished fibrous structure is formed. For example, in typical papermaking processes, the finished fibrous structure is the fibrous structure that is wound on the reel at the end of papermaking, and may subsequently be converted into a finished product, e.g. a sanitary tissue product.

Non-limiting types of fibrous structures according to the present invention include conventionally felt-pressed fibrous structures; pattern densified fibrous structures; and high-bulk, uncompacted fibrous structures. The fibrous structures may be of a homogenous or multilayered (two or three or more layers) construction; and the sanitary tissue products made therefrom may be of a single-ply or multi-ply construction.

In one example, the fibrous structure of the present invention is a pattern densified fibrous structure characterized by having a relatively high-bulk region of relatively low fiber density and an array of densified regions of relatively high fiber density. The high-bulk field is characterized as a field of pillow regions. The densified zones are referred to as knuckle regions. The knuckle regions exhibit greater density than the pillow regions. The densified zones may be discretely spaced within the high-bulk field or may be interconnected, either fully or partially, within the high-bulk field. Typically, from about 8% to about 65% of the fibrous structure surface comprises densified knuckles, the knuckles may exhibit a relative density of at least 125% of the density of the high-bulk field. Processes for making pattern densified fibrous structures are well known in the art as exemplified in U.S. Pat. Nos. 3,301, 746, 3,974,025, 4,191,609 and 4,637,859.

The fibrous structures comprising a trichome in accordance with the present invention may be in the form of through-air-dried fibrous structures, differential density fibrous structures, differential basis weight fibrous structures, wet laid fibrous structures, air laid fibrous structures (examples of which are described in U.S. Pat. Nos. 3,949,035 and 3,825,381), conventional dried fibrous structures, creped or uncreped fibrous structures, patterned-densified or non-patterned-densified fibrous structures, compacted or uncompacted fibrous structures, nonwoven fibrous structures comprising synthetic or multicomponent fibers, homogeneous or multilayered fibrous structures, double re-creped fibrous structures, foreshortened fibrous structures, co-form fibrous structures (examples of which are described in U.S. Pat. No. 4,100,324) and mixtures thereof.

In one example, the air laid fibrous structure is selected from the group consisting of thermal bonded air laid (TBAL) fibrous structures, latex bonded air laid (LBAL) fibrous structures and mixed bonded air laid (MBAL) fibrous structures.

The fibrous structures may exhibit a substantially uniform density or may exhibit differential density regions, in other words regions of high density compared to other regions within the patterned fibrous structure. Typically, when a fibrous structure is not pressed against a cylindrical dryer, such as a Yankee dryer, while the fibrous structure is still wet and supported by a through-air-drying fabric or by another fabric or when an air laid fibrous structure is not spot bonded, the fibrous structure typically exhibits a substantially uniform density.

"Sanitary tissue product" as used herein means a soft, low density (i.e. <about 0.15 g/cm$^3$) web useful as a wiping implement for post-urinary and post-bowel movement cleaning (toilet tissue), for otorhinolaryngological discharges (facial tissue), and multi-functional absorbent and cleaning uses (absorbent towels). The sanitary tissue product may be convolutedly wound upon itself about a core or without a core to form a sanitary tissue product roll.

In one example, the sanitary tissue product of the present invention comprises a fibrous structure according to the present invention.

The sanitary tissue products of the present invention may exhibit a basis weight between about 10 g/m$^2$ to about 120 g/m$^2$ and/or from about 15 g/m$^2$ to about 110 g/m$^2$ and/or from about 20 g/m$^2$ to about 100 g/m$^2$ and/or from about 30 to 90 g/m$^2$. In addition, the sanitary tissue product of the present invention may exhibit a basis weight between about 40 g/m$^2$ to about 120 g/m$^2$ and/or from about 50 g/m$^2$ to about 110 g/m$^2$ and/or from about 55 g/m$^2$ to about 105 g/m$^2$ and/or from about 60 to 100 g/m$^2$ as measured according to the Basis Weight Test Method described herein.

The sanitary tissue products of the present invention may exhibit a total dry tensile of at least 150 g/in and/or from about 200 g/in to about 1000 g/in and/or from about 250 g/in to about 850 g/in as measured according to the Total Dry Tensile Test Method described herein.

In another example, the sanitary tissue product of the present invention may exhibit a total dry tensile of at least 300 g/in and/or at least 350 g/in and/or at least 400 g/in and/or at least 450 g/in and/or at least 500 g/in and/or from about 500 g/in to about 1000 g/in and/or from about 550 g/in to about 850 g/in and/or from about 600 g/in to about 800 g/in as measured according to the Total Dry Tensile Test Method described herein. In one example, the sanitary tissue product exhibits a total dry tensile strength of less than 1000 g/in and/or less than 850 g/in as measured according to the Total Dry Tensile Test Method described herein.

In another example, the sanitary tissue products of the present invention may exhibit a total dry tensile of at least 500 g/in and/or at least 600 g/in and/or at least 700 g/in and/or at least 800 g/in and/or at least 900 g/in and/or at least 1000 g/in and/or from about 800 g/in to about 5000 g/in and/or from about 900 g/in to about 3000 g/in and/or from about 900 g/in to about 2500 g/in and/or from about 1000 g/in to about 2000 g/in as measured according to the Total Dry Tensile Test Method described herein.

"Basis Weight" as used herein is the weight per unit area of a sample reported in lbs/3000 ft$^2$ or g/m$^2$. Basis weight is measured by preparing one or more samples of a certain area (m$^2$) and weighing the sample(s) of a fibrous structure according to the present invention and/or a sanitary tissue product comprising such fibrous structure on a top loading balance with a minimum resolution of 0.01 g. The balance is protected from air drafts and other disturbances using a draft shield. Weights are recorded when the readings on the balance become constant. The average weight (g) is calculated and the average area of the samples (m$^2$) is measured. The basis weight (g/m$^2$) is calculated by dividing the average weight (g) by the average area of the samples (m$^2$).

"Softness" of a fibrous structure according to the present invention and/or a paper product comprising such fibrous structure is determined as follows. Ideally, prior to softness testing, the samples to be tested should be conditioned according to Tappi Method #T4020M-88. Here, samples are preconditioned for 24 hours at a relative humidity level of 10 to 35% and within a temperature range of 22° C. to 40° C. After this preconditioning step, samples should be conditioned for 24 hours at a relative humidity of 48% to 52% and within a temperature range of 22° C. to 24° C. Ideally, the softness panel testing should take place within the confines of a constant temperature and humidity room. If this is not feasible, all samples, including the controls, should experience identical environmental exposure conditions.

Softness testing is performed as a paired comparison in a form similar to that described in "Manual on Sensory Testing Methods", ASTM Special Technical Publication 434, published by the American Society For Testing and Materials 1968 and is incorporated herein by reference. Softness is evaluated by subjective testing using what is referred to as a Paired Difference Test. The method employs a standard external to the test material itself. For tactile perceived softness two samples are presented such that the subject cannot see the samples, and the subject is required to choose one of them on the basis of tactile softness. The result of the test is reported in what is referred to as Panel Score Unit (PSU). With respect to softness testing to obtain the softness data reported herein in PSU, a number of softness panel tests are performed. In each test ten practiced softness judges are asked to rate the relative softness of three sets of paired samples. The pairs of samples are judged one pair at a time by each judge: one sample of each pair being designated X and the other Y. Briefly, each X sample is graded against its paired Y sample as follows:

1. a grade of plus one is given if X is judged to may be a little softer than Y, and a grade of minus one is given if Y is judged to may be a little softer than X;

2. a grade of plus two is given if X is judged to surely be a little softer than Y, and a grade of minus two is given if Y is judged to surely be a little softer than X;

3. a grade of plus three is given to X if it is judged to be a lot softer than Y, and a grade of minus three is given if Y is judged to be a lot softer than X; and, lastly:

4. a grade of plus four is given to X if it is judged to be a whole lot softer than Y, and a grade of minus 4 is given if Y is judged to be a whole lot softer than X.

The grades are averaged and the resultant value is in units of PSU. The resulting data are considered the results of one panel test. If more than one sample pair is evaluated then all sample pairs are rank ordered according to their grades by paired statistical analysis. Then, the rank is shifted up or down in value as required to give a zero PSU value to which ever sample is chosen to be the zero-base standard. The other samples then have plus or minus values as determined by their relative grades with respect to the zero base standard. The number of panel tests performed and averaged is such that about 0.2 PSU represents a significant difference in subjectively perceived softness.

Trichomes

Essentially all plants have trichomes. Those skilled in the art will recognize that some plants will have trichomes of sufficient mass fraction and/or the overall growth rate and/or robustness of the plant so that they may offer attractive agricultural economy to make them more suitable for a large commercial process, such as using them as a source of chemicals, e.g. cellulose, or assembling them into fibrous structures, such as disposable fibrous structures. Trichomes may have a wide range of morphology and chemical properties. For example, the trichomes may be in the form of fibers; namely, trichome fibers. Such trichome fibers may have a high length to diameter ratio.

The following sources are offered as non-limiting examples of trichome-bearing plants (suitable sources) for obtaining trichomes, especially trichome fibers.

Non-limiting examples of suitable sources for obtaining trichomes, especially trichome fibers, are plants in the Labiatae (Lamiaceae) family commonly referred to as the mint family.

Examples of suitable species in the Labiatae family include *Stachys byzantina*, also known as *Stachys lanata* commonly referred to as lamb's ear, woolly betony, or woundwort. The term *Stachys byzantina* as used herein also includes cultivars *Stachys byzantina* 'Primrose Heron', *Stachys byzantina* 'Helene von Stein' (sometimes referred to as *Stachys byzantina* 'Big Ears'), *Stachys byzantina* 'Cotton Boll', *Stachys byzantina* 'Variegated' (sometimes referred to as *Stachys byzantina* 'Striped Phantom'), and *Stachys byzantina* 'Silver Carpet'.

Additional examples of suitable species in the Labiatae family include the *arcticus* subspecies of *Thymus praecox*, commonly referred to as creeping thyme and the *pseudolanuginosus* subspecies of *Thymus praecox*, commonly referred to as wooly thyme.

Further examples of suitable species in the Labiatae family include several species in the genus *Salvia* (sage), including *Salvia leucantha*, commonly referred to as the Mexican bush sage; *Salvia tarahumara*, commonly referred to as the grape scented Indian sage; *Salvia apiana*, commonly referred to as white sage; *Salvia funereal*, commonly referred to as Death Valley sage; *Salvia sagittata*, commonly referred to as balsamic sage; and *Salvia argentiae*, commonly referred to as silver sage.

Even further examples of suitable species in the Labiatae family include *Lavandula lanata*, commonly referred to as wooly lavender; *Marrubium vulgare*, commonly referred to as horehound; *Plectranthus argentatus*, commonly referred to as silver shield; and *Plectranthus tomentosa*.

Non-limiting examples of other suitable sources for obtaining trichomes, especially trichome fibers are plants in the Asteraceae family commonly referred to as the sunflower family.

Examples of suitable species in the Asteraceae family include *Artemisia stelleriana*, also known as silver brocade; *Haplopappus macronema*, also known as the whitestem goldenbush; *Helichrysum petiolare*; *Centaurea maritime*, also known as *Centaurea gymnocarpa* or dusty miller; *Achillea tomentosum*, also known as wooly yarrow; *Anaphalis margaritacea*, also known as pearly everlasting; and *Encelia farinose*, also known as brittle bush.

Additional examples of suitable species in the Asteraceae family include *Senecio brachyglottis* and *Senecio haworthii*, the latter also known as *Kleinia haworthii*.

Non-limiting examples of other suitable sources for obtaining trichomes, especially trichome fibers, are plants in the Scrophulariaceae family commonly referred to as the figwort or snapdragon family.

An example of a suitable species in the Scrophulariaceae family includes *Pedicularis kanei*, also known as the wooly lousewort.

Additional examples of suitable species in the Scrophulariaceae family include the mullein species (*Verbascum*) such as *Verbascum hybridium*, also known as snow maiden; *Verbascum thapsus*, also known as common mullein; *Verbascum baldaccii*; *Verbascum bombyciferum*; *Verbascum broussa*; *Verbascum chaixii*; *Verbascum dumulsum*; *Verbascum laciniatum*; *Verbascum lanatum*; *Verbascum longifolium*; *Verbascum lychnitis*; *Verbascum olympicum*; *Verbascum paniculatum*; *Verbascum phlomoides*; *Verbascum phoeniceum*; *Verbascum speciosum*; *Verbascum thapsiforme*; *Verbascum virgatum*; *Verbascum wiedemannianum*; and various mullein hybrids including *Verbascum* 'Helen Johnson' and *Verbascum* 'Jackie'.

Further examples of suitable species in the Scrophulariaceae family include *Stemodia tomentosa* and *Stemodia durantifolia*.

Non-limiting examples of other suitable sources for obtaining trichomes, especially trichome fibers include *Greyia radlkoferi* and *Greyia flanmaganii* plants in the Greyiaceae family commonly referred to as the wild bottlebrush family.

Non-limiting examples of other suitable sources for obtaining trichomes, especially trichome fibers include members of the Fabaceae (legume) family. These include the *Glycine max*, commonly referred to as the soybean, and *Trifolium pratense* L, commonly referred to as medium and/or mammoth red clover.

Non-limiting examples of other suitable sources for obtaining trichomes, especially trichome fibers include members of the Solanaceae family including varieties of *Lycopersicum esculentum*, otherwise known as the common tomato.

Non-limiting examples of other suitable sources for obtaining trichomes, especially trichome fibers include members of the Convolvulaceae (morning glory) family, including *Argyreia nervosa*, commonly referred to as the wooly morning glory and *Convolvulus cneorum*, commonly referred to as the bush morning glory.

Non-limiting examples of other suitable sources for obtaining trichomes, especially trichome fibers include members of the Malvaceae (mallow) family, including *Anoda cristata*, commonly referred to as spurred anoda and *Abutilon theophrasti*, commonly referred to as velvetleaf.

Non-limiting examples of other suitable sources for obtaining trichomes, especially trichome fibers include *Buddleia marrubiifolia*, commonly referred to as the wooly butterfly bush of the Loganiaceae family; the *Casimiroa tetrameria*, commonly referred to as the wooly leafed sapote of the Rutaceae family; the *Ceanothus tomentosus*, commonly referred to as the wooly leafed mountain liliac of the Rhamnaceae family; the 'Philippe Vapelle' cultivar of *renardii* in the Geraniaceae (*geranium*) family; the *Tibouchina urvilleana*, commonly referred to as the Brazilian spider flower of the Melastomataceae family; the *Tillandsia recurvata*, commonly referred to as ballmoss of the Bromeliaceae (pineapple) family; the *Hypericum tomentosum*, commonly referred to as the wooly St. John's wort of the Hypericaceae family; the *Chorizanthe orcuttiana*, commonly referred to as the San Diego spineflower of the Polygonaceae family; *Eremocarpus setigerus*, commonly referred to as the doveweed of the Euphorbiaceae or spurge family; *Kalanchoe tomentosa*, commonly referred to as the panda plant of the Crassulaceae family; and *Cynodon dactylon*, commonly referred to as Bermuda grass, of the Poaceae family; and *Congea tomentosa*, commonly referred to as the shower orchid, of the Verbenaceae family.

Suitable trichome-bearing plants are commercially available from nurseries and other plant-selling commercial venues. For example, *Stachys byzantina* may be purchased and/or viewed at Blanchette Gardens, Carlisle, Mass.

The trichome-bearing material may be subjected to a mechanical process to liberate its trichomes from its plant epidermis to enrich the pulp or fiber mass' content of individualized trichomes. This may be carried out by means of screening or air classifying equipment well known in the art. A suitable air classifier is the Hosokawa Alpine 50ATP, sold by Hosokawa Micron Powder Systems of Summit, N.J. Other suitable classifiers are available from the Minox Siebtechnik.

In one example, a trichome suitable for use in the fibrous structures of the present invention comprises cellulose.

In yet another example, a trichome suitable for use in the fibrous structures of the present invention comprises a fatty acid.

In still another example, a trichome suitable for use in the fibrous structures of the present invention is hydrophobic.

In yet another example, a trichome suitable for use in the fibrous structures of the present invention is less hydrophilic that softwood fibers. This characteristic of the trichome may facilitate a reduction in drying temperatures needed to dry fibrous structures comprising such trichome and/or may facilitate making the fibrous structures containing such trichome at a faster rate.

Figure 2:
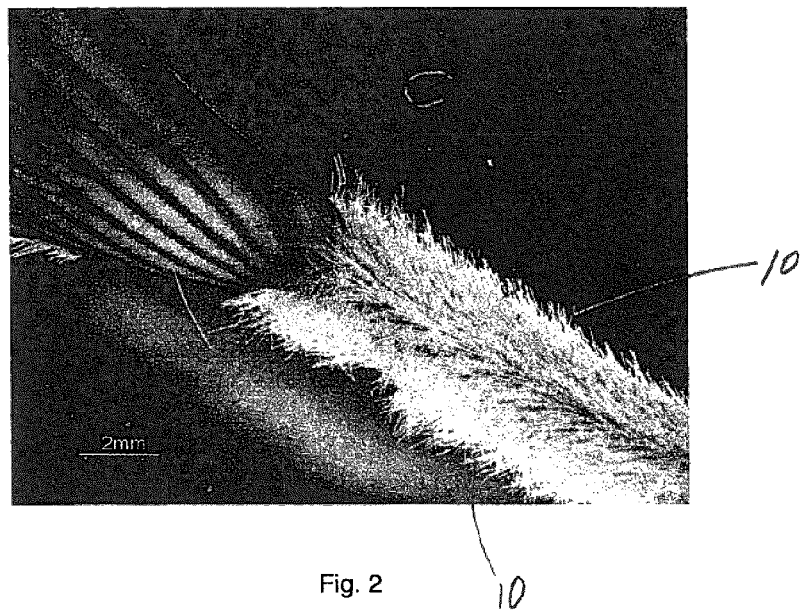
FIG. 2 is a light micrograph of a lower stem illustrating trichomes present on red clover, *Trifolium pratense* L.

As shown in FIG. 1, numerous trichomes 10 are present on this red clover leaf and leaf stem. FIG. 2 shows numerous trichomes 10 present on a red clover lower stem.

Figure 3:
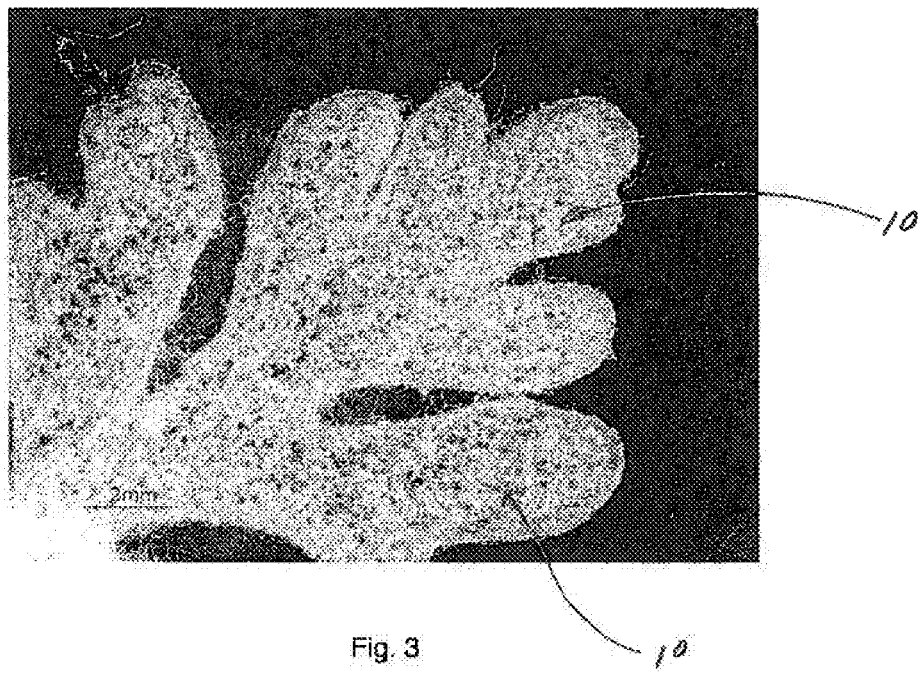
FIG. 3 is a light micrograph of a leaf illustrating trichomes present on dusty miller, *Centaurea gymnocarpa;*
Figure 4:
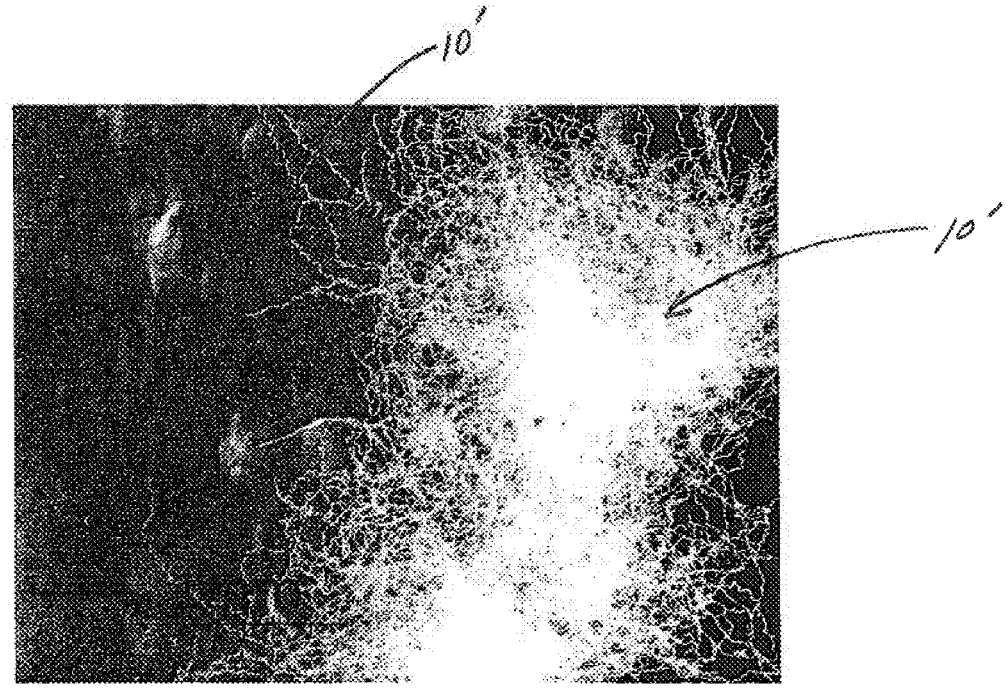
FIG. 4 is a light micrograph of individualized trichomes individualized from a leaf of dusty miller, *Centaurea gymnocarpa;*

As shown in FIG. 3, a dusty miller leaf is contains numerous trichomes 10. FIG. 4 shows individualized trichomes 10' obtained from a dusty miller leaf.

Figure 5:
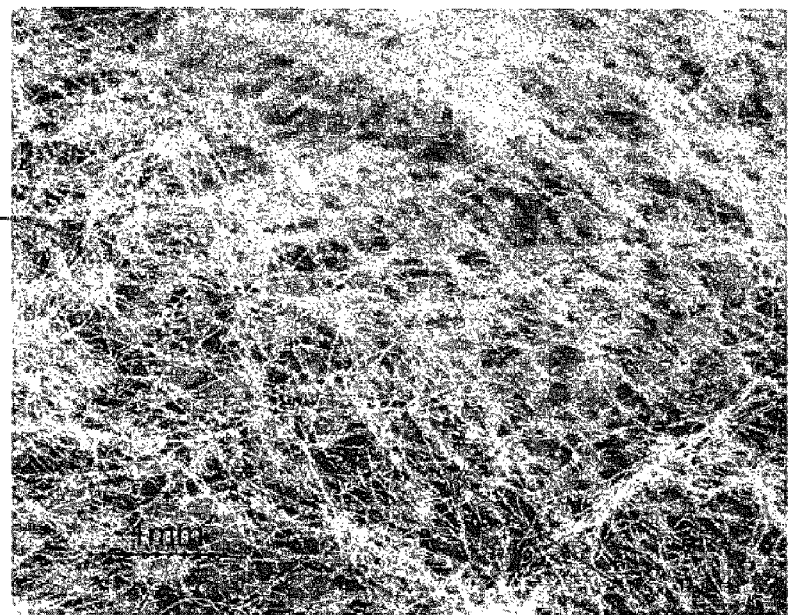
FIG. 5 is a light micrograph of a basal leaf illustrating trichomes present on silver sage, *Salvia argentiae;*
Figure 6:
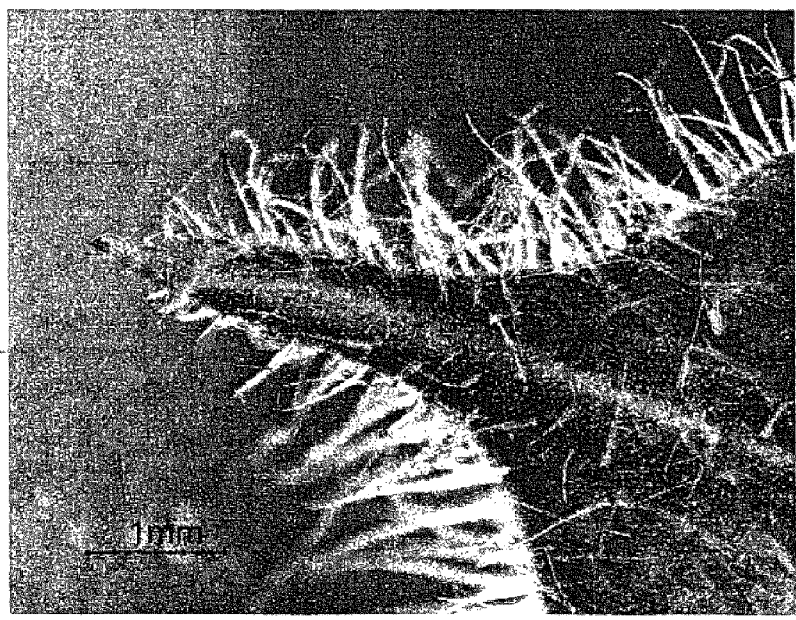
FIG. 6 is a light micrograph of a bloom-stalk leaf illustrating trichomes present in silver sage, *Salvia argentiae;*

As shown in FIG. 5, a basal leaf on a silver sage contains numerous trichomes 10. FIG. 6 shows trichomes 10 present on a bloom-stalk leaf of a silver sage.

Figure 7:
FIG. 7 is a light micrograph of a mature leaf illustrating trichomes present on common mullein, *Verbascum thapsus;*
Figure 8:
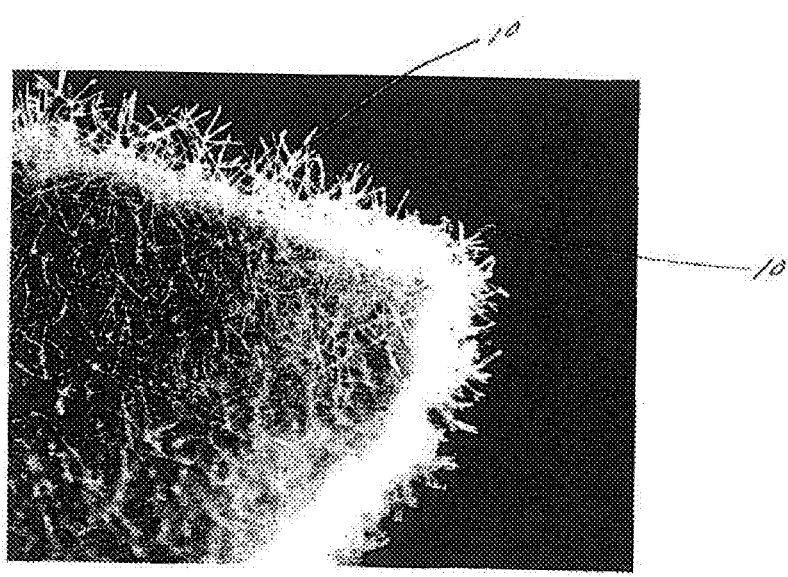
FIG. 8 is a light micrograph of a juvenile leaf illustrating trichomes present on common mullein, *Verbascum thapsus;*

As shown in FIG. 7, trichomes 10 are present on a mature leaf of common mullein. FIG. 8 shows trichomes 10 present on a juvenile leaf of common mullein.

Figure 9:
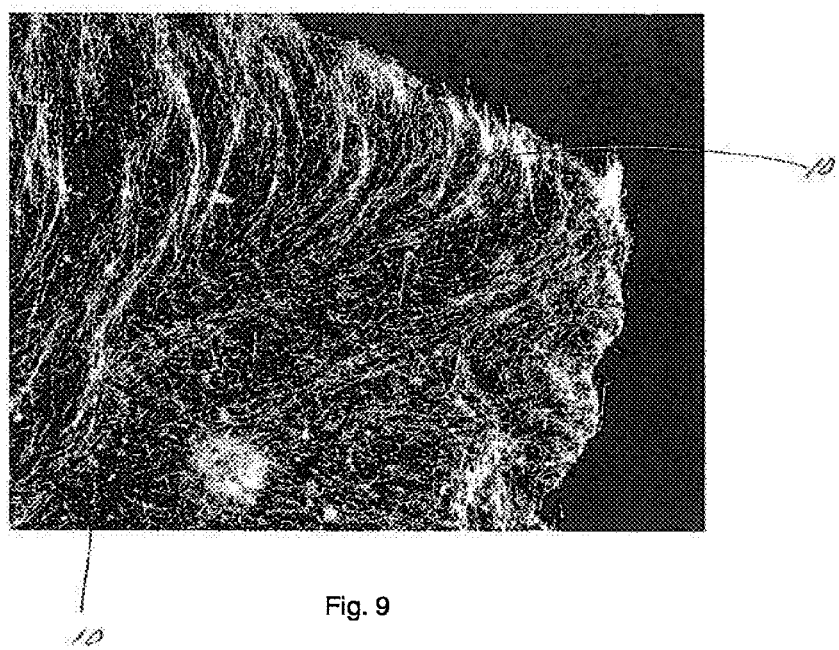
FIG. 9 is a light micrograph of a perpendicular view of a leaf illustrating trichomes present on wooly betony, *Stachys byzantina;*
Figure 10:
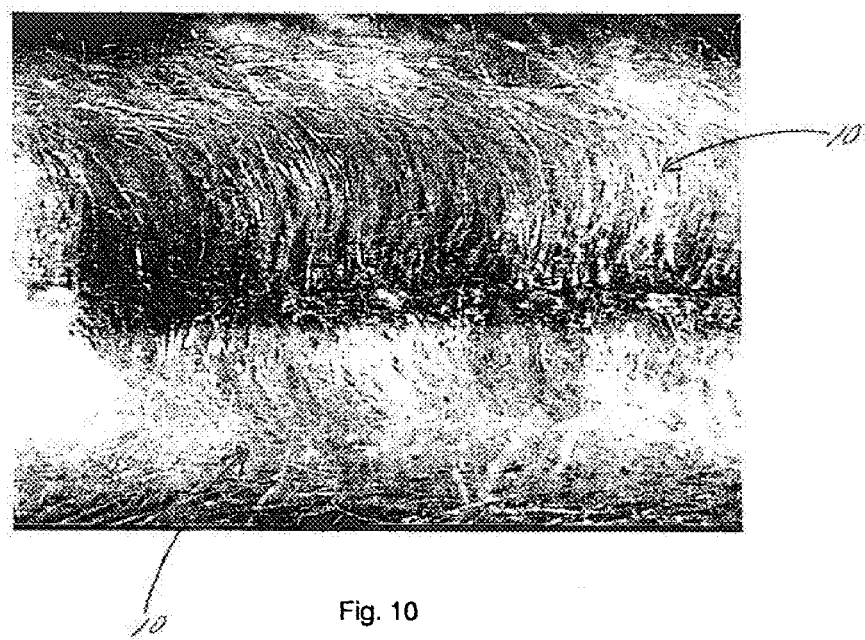
FIG. 10 is a light micrograph of a cross-sectional view of a leaf illustrating trichomes present on wooly betony, *Stachys byzantina.
Figure 11:
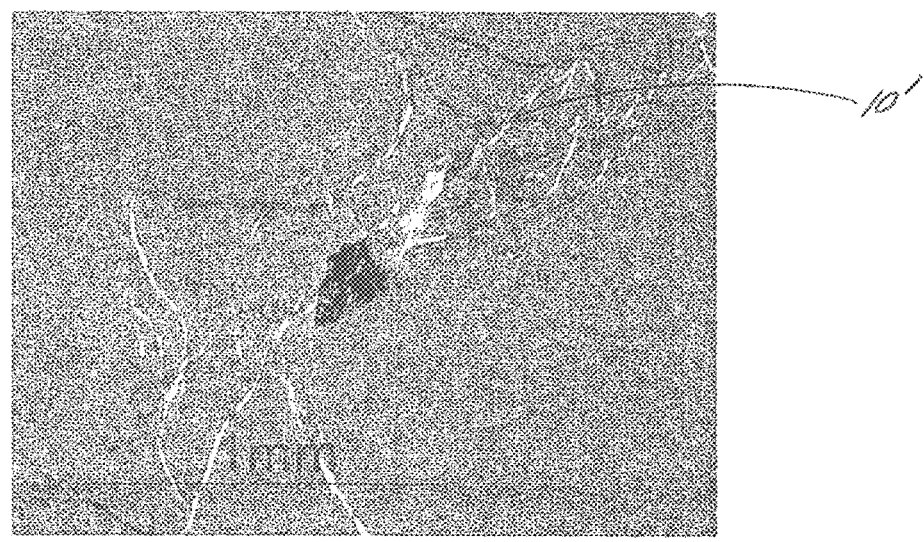
* and FIG. 11 is a light micrograph of individualized trichomes in the form of a plurality of trichomes bound by their individual attachment to a common remnant of a host plant, wooly betony, *Stachys byzantina*.

FIG. 9 shows, via a perpendicular view, trichomes 10 present on a leaf of wooly betony. FIG. 10 is a cross-sectional view of a leaf of wooly betony containing trichomes 10. FIG. 11 shows individualized trichomes 10' obtained from a wooly betony leaf.

Table 1 below shows a comparison of fiber morphology for a hardwood fiber (Eucalyptus pulp fiber), a softwood fiber (NSK pulp fiber) and a trichome fiber.

TABLE 1

| Property | Eucalyptus Fiber | NSK Fiber | Trichome Fiber |
|---|---|---|---|
| Fiber Length (mm) | 0.76 | 2.18 | 1.352 |
| Fiber Width (μm) | 19.1 | 27.6 | 18.1 |
| Coarseness (mg/m) | 0.0895 | 0.1386 | 0.0995 |
| Bendability | 3.4 | 6.4 | 0.5 |
| Kinks/mm | 0.82 | 0.47 | 0.77 |
| Kajaani Cell Wall | 6.6 | 9.6 | 6.44 |

As is evident from Table 1, trichome fibers are greater in length than Eucalyptus fibers, but shorter than NSK fibers. However, other properties of trichome fibers are more closely associated with properties of Eucalyptus fibers than to NSK fibers.

Fibrous Structures

The fibrous structures of the present invention may comprise greater than 50% and/or greater than 75% and/or greater than 90% and/or 100% or less by weight on a dry fiber basis of pulp fibers.

In one example, the fibrous structures of the present invention comprise less than 22% and/or less than 21% and/or less than 20% and/or less than 19% and/or less than 18% and/or to about 5% and/or to about 7% and/or to about 10% and/or to about 12% and/or to about 15% by weight on a dry fiber basis of softwood fibers.

In one example, the fibrous structures of the present invention may exhibit a basis weight between about 10 $g/m^2$ to about 120 $g/m^2$ and/or from about 15 $g/m^2$ to about 110 $g/m^2$ and/or from about 20 $g/m^2$ to about 100 $g/m^2$ and/or from about 30 to 90 $g/m^2$. In addition, the sanitary tissue product of the present invention may exhibit a basis weight between about 40 $g/m^2$ to about 120 $g/m^2$ and/or from about 50 $g/m^2$ to about 110 $g/m^2$ and/or from about 55 $g/m^2$ to about 105 $g/m^2$ and/or from about 60 to 100 $g/m^2$ as measured according to the Basis Weight Test Method described herein.

In another example, the fibrous structures of the present invention may exhibit a basis weight of at least 21 $g/m^2$ and/or at least 23 $g/m^2$ and/or at least 25 $g/m^2$.

In yet another example, the fibrous structures of the present invention may comprise a plurality of pulp fibers, wherein greater than 0% but less than 20% by weight on a dry fiber basis of the pulp fibers are softwood fibers and wherein the fibrous structure comprises pulp fibers derived from a pulp fiber-producing source that has a growing cycle of less than 800 and/or every 400 and/or every 200 and/or every 100 or less days.

The fibrous structures of the present invention may comprise one or more individualized trichomes, especially trichome fibers. In one example, a trichome fiber suitable for use in the fibrous structures of the present invention exhibit a fiber length of from about 100 μm to about 7000 μm and a width of from about 3 μm to about 30 μm.

In addition to a trichome, other fibers and/or other ingredients may also be present in the fibrous structures of the present invention.

Fibrous structures according to this invention may contain from about 0.1% to about 100% and/or from about 0.5% to about 90% and/or from about 0.5% to about 80% and/or from about 0.5% to about 50% and/or from about 1% to about 40% and/or from about 2% to about 30% and/or from about 5% to about 25% by weight on a dry fiber basis of trichome fibers.

In addition to a trichome, the fibrous structure may comprise other additives, such as wet strength additives, softening additives, solid additives (such as starch, clays), dry strength resins, wetting agents, lint resisting and/or reducing agents, absorbency-enhancing agents, immobilizing agents, especially in combination with emollient lotion compositions, antiviral agents including organic acids, antibacterial agents, polyol polyesters, antimigration agents, polyhydroxy plasticizers and mixtures thereof. Such other additives may be added to the fiber furnish, the embryonic fibrous web and/or the fibrous structure.

Such other additives may be present in the fibrous structure at any level based on the dry weight of the fibrous structure.

The other additives may be present in the fibrous structure at a level of from about 0.001 to about 50% and/or from about 0.001 to about 20% and/or from about 0.01 to about 5% and/or from about 0.03 to about 3% and/or from about 0.1 to about 1.0% by weight, on a dry fibrous structure basis.

The fibrous structures of the present invention may be subjected to any suitable post processing including, but not limited to, printing, embossing, calendaring, slitting, folding, combining with other fibrous structures, and the like.

Table 2 below shows a comparison of fibrous structures according to the present invention that comprise trichome fibers that have been classified using a classifier from Minox Siebtechnik and a control fibrous structure without any trichome fibers.

TABLE 2

| Property | Control 1 | 2.5% Trichome Fibers | 5% Trichome Fibers | 7.5% Trichome Fibers |
|---|---|---|---|---|
| Basis Weight | 29.4 | 29.2 | 29.0 | 30.0 |
| Softwood/Hardwood/ Trichome (%) | 26/74/0 | 19/78.5/2.5 | 17/78/5 | 17/75.5/7.5 |
| Total Dry Tensile (g/in) | 550.7 | 550.7 | 535.3 | 663.3 |
| Softness (PSU) | 0.5 | 1.06 | 1.49 | 1.39 |

Table 3 below shows a comparison of fibrous structures according to the present invention that comprise trichome fibers that have been classified using a classifier from Hosokawa and a control fibrous structure without any trichome fibers.

TABLE 3

| Property | Control 1 | 2.5% Trichome Fibers | 5% Trichome Fibers | 7.5% Trichome Fibers |
|---|---|---|---|---|
| Basis Weight | 28.9 | 28.8 | 28.1 | 28.6 |
| Softwood/Hardwood/ Trichome (%) | 24/76/0 | 19/78.5/2.5 | 17/78/5 | 18/74.5/7.5 |
| Total Dry Tensile (g/in) | 566.0 | 523.0 | 523.0 | 544.7 |
| Softness (PSU) | −0.44 | 0.67 | 1.05 | 1.66 |

As shown in Tables 2 and 3, the use of trichome fibers in the fibrous structure making process permits the reduction of softwood fibers in the fibrous structure. In one example, the inclusion of trichome fibers permits at least a 5% by weight on a dry fiber basis reduction of softwood fibers while maintaining a total dry tensile strength of greater than 500 g/in and/or greater than 520 g/in and increasing the softness (PSU) to at least 0.67 and/or at least 1.00.

In one example, the replacement of softwood fibers with trichome fibers produces a fibrous structure and/or sanitary tissue product that exhibits a softness (PSU) increase of at least 0.5 and/or at least 0.67 and/or at least 1.00 compared to the same fibrous structure and/or sanitary tissue product without the trichome fibers.

In addition to the reduction of softwood fibers, the inclusion of trichome fibers, may result, especially when they are added to an outer layer or in a homogeneous fibrous structure, in a surface that has a "fuzzy" feel to consumers. In addition, the trichome fibers may also provide surface smoothness increases, strength increases and flexibility increases to the fibrous structures. The trichome fibers in one example at 5% inclusion, results in a reduction of Slip-and-Stick Coefficient of Friction of at least 15% and/or at least 17% and/or at least 20% and/or at least 22% as shown in Table 4 below. These Slip-and-Stick Coefficients of Friction are significant and large and indicate a very smooth surface feel versus substrates without trichome fibers.

TABLE 4

| | CONTROL W/O TRICHOME FIBERS (AVG) | WITH TRICHOME FIBERS (AVG) | % change |
|---|---|---|---|
| COF frit kinetic-out | 0.968 | 0.770 | 20.41% |
| COF frit kinetic-in | 1.003 | 0.784 | 21.80% |
| COF frit kinetic-AVG | 0.985 | 0.777 | 21.12% |
| COF frit slipstick-out | 250 | 201 | 19.60% |
| COF frit slipstick-in | 281 | 194 | 30.84% |
| COF frit slipstick-AVG | 265 | 198 | 25.54% |
| COF kinetic*slipstick | 261 | 153 | 41.27% |

Processes for Making Trichome-Containing Fibrous Structures

Any suitable process for making fibrous structures known in the art may be used to make trichome-containing fibrous structures of the present invention.

In one example, the trichome-containing fibrous structures of the present invention are made by a wet laid fibrous structure making process.

In another example, the trichome-containing fibrous structures of the present invention are made by an air laid fibrous structure making process.

In one example, a trichome-containing fibrous structure is made by the process comprising the steps of: a) preparing a fiber furnish (slurry) by mixing a trichome with water; b) depositing the fiber furnish on a foraminous forming surface to form an embryonic fibrous web; and c) drying the embryonic fibrous web.

In one example, a fiber furnish comprising a trichome, such as a trichome fiber, is deposited onto a foraminuous forming surface via a headbox.

NON-LIMITING EXAMPLES

Example 1

Fibrous Structure without Trichomes

The following example illustrates a non-limiting example for the preparation of a non-trichome containing fibrous structure on a pilot-scale Fourdrinier paper making machine.

A sheet with 33%×34%×33% layering consist of fabric layer, center layer and wire layer. The entire sheet has 70% by weight on a dry fiber basis of Eucalyptus and 30% by weight on a dry fiber basis of NSK pulp fibers is made.

An aqueous slurry of eucalyptus fibers is prepared at about 3% by weight using a conventional repulper. Separately, an aqueous slurry of NSK fibers of about 3% by weight is made up using a conventional repulper.

In order to impart temporary wet strength to the finished fibrous structure, a 1% dispersion of temporary wet strengthening additive (e.g., Parez° commercially available from Kemira) is prepared and is added to the NSK fiber stock pipe at a rate sufficient to deliver 0.3% temporary wet strengthening additive based on the dry weight of the NSK fibers. The absorption of the temporary wet strengthening additive is enhanced by passing the treated slurry through an in-line mixer.

The eucalyptus fiber slurry is diluted with white water at the inlet of a fan pump to a consistency of about 0.15% based on the total weight of the eucalyptus fiber slurry. The NSK fibers, likewise, are diluted with white water at the inlet of a fan pump to a consistency of about 0.15% based on the total weight of the NSK fiber slurry. The eucalyptus fiber slurry and the NSK fiber slurry are both directed to a layered headbox capable of maintaining the slurries as separate streams until they are deposited onto a forming fabric on the Fourdrinier.

"DC 2310" (Dow Corning, Midland, Mich.) antifoam is dripped into the wirepit to control foam to maintain whitewater levels of 10 ppm.

The paper making machine has a layered headbox with a top chamber, a center chamber, and a bottom chamber. The eucalyptus fiber slurry is pumped through the top and bottom headbox chambers and, simultaneously, the NSK fiber slurry is pumped through the center headbox chamber and delivered in superposed relation onto a Fourdrinier wire to form thereon a three-layer embryonic web, of which about 70% is made up of the eucalyptus fibers and about 30% is made up of the NSK fibers. Dewatering occurs through the Fourdrinier wire and is assisted by a deflector and vacuum boxes. The Fourdrinier wire is of a 5-shed, satin weave configuration having 87 machine-direction and 76 cross-machine-direction monofilaments per inch, respectively. The speed of the Fourdrinier wire is about 750 fpm (feet per minute).

The embryonic wet web is transferred from the Fourdrinier wire, at a fiber consistency of about 15% at the point of transfer, to a patterned drying fabric. The speed of the patterned drying fabric is about the same as the speed of the Fourdrinier wire. The drying fabric is designed to yield a pattern densified tissue with discontinuous low-density deflected areas arranged within a continuous network of high density (knuckle) areas. This drying fabric is formed by casting an impervious resin surface onto a fiber mesh supporting fabric. The supporting fabric is a 98×62 filament, dual layer mesh. The thickness of the resin cast is about 12 mils above the supporting fabric. A suitable process for making the patterned drying fabric is described in published application US 2004/0084167 A1.

Further de-watering is accomplished by vacuum assisted drainage until the web has a fiber consistency of about 30%.

While remaining in contact with the patterned drying fabric, the web is pre-dried by air blow-through pre-dryers to a fiber consistency of about 65% by weight.

After the pre-dryers, the semi-dry web is transferred to the Yankee dryer and adhered to the surface of the Yankee dryer with a sprayed creping adhesive. The creping adhesive is an aqueous dispersion with the actives consisting of about 22% polyvinyl alcohol, about 11% CREPETROL A3025, and about 67% CREPETROL R6390. CREPETROL A3025 and CREPETROL R6390 are commercially available from Hercules Incorporated of Wilmington, Del. The creping adhesive is delivered to the Yankee surface at a rate of about 0.15% adhesive solids based on the dry weight of the web. The fiber consistency is increased to about 97% before the web is dry creped from the Yankee with a doctor blade.

The doctor blade has a bevel angle of about 25 degrees and is positioned with respect to the Yankee dryer to provide an impact angle of about 81 degrees. The Yankee dryer is operated at a temperature of about 350° F. and a speed of about 800 fpm. The fibrous structure is wound in a roll using a surface driven reel drum having a surface speed of about 656 feet per minute. The fibrous structure may be subsequently converted into a two-ply sanitary tissue product having a basis weight of about 50 lbs/3000 ft$^2$.

The resulting total dry tensile strength for the fibrous structure product having no trichomes is 566 g/in.

Example 2

Fibrous Structure with Trichome Fibers

This following example illustrates a non-limiting example for the preparation of a fibrous structure according to the present invention on a pilot-scale Fourdrinier paper making machine with the addition of trichome fibers providing a strength increase.

The following Example illustrates a non-limiting example for the preparation of sanitary tissue product comprising a fibrous structure according to the present invention on a pilot-scale Fourdrinier fibrous structure making machine.

Individualized trichome are first prepared from *Stachys byzantina* bloom stalks consisting of the dried stems, leaves, and pre-flowering buds, by passing dried *Stachys byzantina* plant matter through a knife cutter (Wiley mill, manufactured by the C. W. Brabender Co. located in South Hackensack, N.J.) equipped with an attrition screen having ¼" holes. Exiting the Wiley mill is a composite fluff constituting the individualized trichome fibers together with chunks of leaf and stem material. The individualized trichome fluff is then passed through an air classifier (Hosokawa Alpine 50ATP); the "accepts" or "fine" fraction from the classifier is greatly enriched in individualized trichome fibers while the "rejects" or "coarse" fraction is primarily chunks of stalks, and leaf elements with only a minor fraction of individualized trichome fibers. A squirrel cage speed of 9000 rpm, an air pressure resistance of 10-15 mbar, and a feed rate of about 10 g/min are used on the 50 ATP. The resulting individualized trichome material (fines) is mixed with a 10% aqueous dispersion of "Texcare 4060" to add about 10% by weight "Texcare 4060" by weight of the bone dry weight of the individualized trichomes followed by slurrying the "Texcare"-treated trichome in water at 3% consistency using a conventional repulper. This slurry is passed through a stock pipe toward another stock pipe containing a eucalyptus fiber slurry.

Special care must be taken while processing the trichomes. 60 lbs. of trichome fiber is pulped in a 50 gallon pulper by adding water in half amount required to make a 1% trichome fiber slurry. This is done to prevent trichome fibers over flowing and floating on surface of the water due to lower density and hydrophobic nature of the trichome fiber. After mixing and stirring a few minutes, the pulper is stopped and the remaining trichome fibers are pushed in while water is added. After pH adjustment, it is pulped for 20 minutes, then dumped in a separate chest for delivery onto the machine headbox. This allows one to place trichome fibers in one or more layers, alone or mixed with other fibers, such as hardwood fibers and/or softwood fibers. During this particular run, the trichome fibers are added exclusively on the wire outer layer as the product is converted wire side up; therefore it is desirable to add the trichome fibers to the wire side (the side where the tactile feel senses paper the most).

The aqueous slurry of eucalyptus fibers is prepared at about 3% by weight using a conventional repulper. This slurry is also passed through a stock pipe toward the stock pipe containing the trichome fiber slurry.

The 1% trichome fiber slurry is combined with the 3% eucalyptus fiber slurry in a proportion which yields about 13.3% trichome fibers and 86.7% eucalyptus fibers. The stockpipe containing the combined trichome and eucalyptus fiber slurries is directed toward the wire layer of headbox of a Fourdrinier machine.

Separately, an aqueous slurry of NSK fibers of about 3% by weight is made up using a conventional repulper.

In order to impart temporary wet strength to the finished fibrous structure, a 1% dispersion of temporary wet strengthening additive (e.g., Parez® commercially available from Kemira) is prepared and is added to the NSK fiber stock pipe at a rate sufficient to deliver 0.3% temporary wet strengthening additive based on the dry weight of the NSK fibers. The absorption of the temporary wet strengthening additive is enhanced by passing the treated slurry through an in-line mixer.

The trichome fiber and eucalyptus fiber slurry is diluted with white water at the inlet of a fan pump to a consistency of about 0.15% based on the total weight of the eucalyptus and trichome fiber slurry. The NSK fibers, likewise, are diluted with white water at the inlet of a fan pump to a consistency of about 0.15% based on the total weight of the NSK fiber slurry. The eucalyptus/trichome fiber slurry and the NSK fiber slurry are both directed to a layered headbox capable of maintaining the slurries as separate streams until they are deposited onto a forming fabric on the Fourdrinier.

"DC 2310" antifoam is dripped into the wirepit to control foam to maintain whitewater levels of 10 ppm of antifoam.

The fibrous structure making machine has a layered headbox having a top chamber, a center chamber, and a bottom chamber. The eucalyptus/trichome combined fiber slurry is pumped through the top headbox chamber, eucalyptus fiber slurry is pumped through the bottom headbox chamber, and, simultaneously, the NSK fiber slurry is pumped through the center headbox chamber and delivered in superposed relation onto the Fourdrinier wire to form thereon a three-layer embryonic web, of which about 83% is made up of the eucalyptus/trichome fibers and 17% is made up of the NSK fibers. Dewatering occurs through the Fourdrinier wire and is assisted by a deflector and vacuum boxes. The Fourdrinier wire is of a 5-shed, satin weave configuration having 87 machine-direction and 76 cross-machine-direction monofilaments per inch, respectively. The speed of the Fourdrinier wire is about 750 fpm (feet per minute).

The embryonic wet web is transferred from the Fourdrinier wire, at a fiber consistency of about 15% at the point of transfer, to a patterned drying fabric. The speed of the patterned drying fabric is the same as the speed of the Fourdrinier wire. The drying fabric is designed to yield a pattern densified tissue with discontinuous low-density deflected areas arranged within a continuous network of high density (knuckle) areas. This drying fabric is formed by casting an impervious resin surface onto a fiber mesh supporting fabric. The supporting fabric is a 45×52 filament, dual layer mesh. The thickness of the resin cast is about 12 mils above the supporting fabric. A suitable process for making the patterned drying fabric is described in published application US 2004/0084167 A1.

Further de-watering is accomplished by vacuum assisted drainage until the web has a fiber consistency of about 30%.

While remaining in contact with the patterned drying fabric, the web is pre-dried by air blow-through pre-dryers to a fiber consistency of about 65% by weight.

After the pre-dryers, the semi-dry web is transferred to the Yankee dryer and adhered to the surface of the Yankee dryer with a sprayed creping adhesive. The creping adhesive is an aqueous dispersion with the actives consisting of about 22% polyvinyl alcohol, about 11% CREPETROL A3025, and about 67% CREPETROL R6390. CREPETROL A3025 and CREPETROL R6390 are commercially available from Hercules Incorporated of Wilmington, Del. The creping adhesive is delivered to the Yankee surface at a rate of about 0.15% adhesive solids based on the dry weight of the web. The fiber consistency is increased to about 97% before the web is dry creped from the Yankee with a doctor blade.

The doctor blade has a bevel angle of about 25 degrees and is positioned with respect to the Yankee dryer to provide an impact angle of about 81 degrees. The Yankee dryer is operated at a temperature of about 350° F. (177° C.) and a speed of about 800 fpm. The fibrous structure is wound in a roll using a surface driven reel drum having a surface speed of about 656 feet per minute. The fibrous structure may be subsequently converted into a two-ply sanitary tissue product having a basis weight of about 50 g/m².

5% by weight of trichome fibers on the outer layer of the sheet produced a product with considerable softness. To control tensile, softwood fibers had to be removed by 7% to compensate for 5% addition of trichome fibers. The base product had a softness of −0.44 PSU compared to our standard but the fibrous structure made with trichome fibers had 1.05 PSU at a comparable wet and dry tensile. Adjusting for the base softness deficit the condition with trichome fibers softness would be at about 1.5 PSU. Other benefits of trichome fiber addition is that the pre-dryer temperatures may be reduced by at least 30° F., and in one example at least 30° F. to about 50° F. This is a significant temperature reduction that can be used for energy saving or increase machine capacity if it is drying limited. In addition to the benefits described above, the use of trichome fibers to reduce the use of pulp fibers, especially softwood pulp fibers, in making fibrous structures, such as sanitary tissue products, also has environmental benefits, such as reducing carbon footprint of fibrous structures, especially paper products that have historically been made from wood pulp, by reducing the usage wood pulp and thus tree usage while maintaining or increasing the softness of the fibrous structures. In addition, as is always clear from the above description, the use of trichome fibers in fibrous structure breaks the strength/softness contradiction that has historically plagued the fibrous structure, especially the sanitary tissue product industry by increasing strength while increasing softness of the fibrous structure.

The following table, Table 5, shows the results for the fibrous structure of Example 2:

TABLE 5

|  | Control (No Trichome Fibers) | 5% Trichome Fibers |
|---|---|---|
| SW % used | 24 | 17 |
| Total Tensile (gm/in) | 566 | 523 |
| Softness | −0.4 | 1.05 |

Test Methods

Unless otherwise specified, all tests described herein including those described under the Definitions section and the following test methods are conducted on samples that have been conditioned in a conditioned room at a temperature of 73° F.±4° F. (about 23° C.±2.2° C.) and a relative humidity of 50%±10% for 2 hours prior to the test. All tests are conducted in such conditioned room. Do not test samples that have defects such as wrinkles, tears, holes, and like.

Total Dry Tensile Strength Test Method

Cut at least eight 1 inch wide strips of the fibrous structure and/or sanitary tissue product to be tested in the machine direction. Cut at least eight 1 inch wide strips in the cross direction. If the machine direction and cross direction are not readily ascertainable, then the cross direction will be the strips that result in the lower peak load tensile. For the wet measurements, each sample is wetted by submerging the sample in a distilled water bath for 30 seconds. The wet property of the wet sample is measured within 30 seconds of removing the sample from the bath.

For the actual measurements of the properties, use a Thwing-Albert Intelect II Standard Tensile Tester (Thwing-Albert Instrument Co. of Philadelphia, Pa.). Insert the flat face clamps into the unit and calibrate the tester according to the instructions given in the operation manual of the Thwing-Albert Intelect II. Set the instrument crosshead speed to 4.00 in/min and the 1st and 2nd gauge lengths to 4.00 inches. The break sensitivity is set to 20.0 grams and the sample width is set to 1.00 inch. The energy units are set to TEA and the tangent modulus (Modulus) trap setting is set to 38.1 g.

After inserting the fibrous structure sample strip into the two clamps, the instrument tension can be monitored. If it shows a value of 5 grams or more, the fibrous structure sample strip is too taut. Conversely, if a period of 2-3 seconds passes after starting the test before any value is recorded, the fibrous structure sample strip is too slack.

Start the tensile tester as described in the tensile tester instrument manual. When the test is complete, read and record the following with units of measure:

Peak Load Tensile (Tensile Strength) (g/in)
Peak Elongation (Elongation) (%)
Peak CD TEA (Wet CD TEA) (in-g/in$^2$)
Tangent Modulus (Dry MD Modulus and Dry CD Modulus) (at 15 g/cm)

Test each of the samples in the same manner, recording the above measured values from each test. Average the values for each property obtained from the samples tested to obtain the reported value for that property.

Total Dry Tensile (TDT)=Peak Load MD Tensile (g/in)+Peak Load CD Tensile (g/in)

Slip-and-Stick Coefficient of Friction Test Method

The Slip-and-Stick Coefficient of Friction is defined as the mean deviation of the coefficient of friction. It is dimensionless. This test is performed on a KES-FB4 Surface Analyzer from Kato Tekko Co. of Karato-Cho, Nishikiyo, Minami-Ku, Koyota, Japan, with a modified friction probe. The probe sled is a two centimeter diameter, 40 to 60 micron glass frit obtained from Ace Glass Company. The normal force of the probe was 12.5 grams. The details of the procedure are described in "Methods for the Measurement of the Mechanical Properties of Tissue Paper" by Ampulski, et. al., 1991 International Paper Physics Conference, page 19, incorporated herein by reference. When a sample is scanned, the instrument senses the lateral force on the stylus as the sample is scanned. The lateral force is called the frictional force; and the ratio of the frictional force to stylus weight is the coefficient of friction, mu. The instrument then solves the following equation to determine Slip-and-Stick Coefficient of Friction for each scan of each sample.

$$\text{Slip-and-Stick Coefficient of Friction} = \frac{1}{X} \int_0^X |m\mu_{avg} - m\mu| \, dx$$

in which mμ is the ratio of frictional force to probe loading; mμ$_{avg}$ is the average value of mμ; and X is 2 cm.

The samples are scanned in both the forward and reverse direction. The average values from the forward and reverse scans of multiple samples were obtained and reported.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A layered fibrous structure exhibiting a basis weight of from about 10 to about 120 g/m$^2$, wherein the fibrous structure comprises greater than 50% by weight on a dry fiber basis of pulp fibers, wherein greater than 0% but less than 20% by weight on a dry fiber basis of the pulp fibers are softwood fibers, wherein the pulp fibers comprise trichome fibers, wherein one or more of the trichome fibers are derived from a plant in the *Stachys* genus, and wherein one or more of the trichome fibers are derived from a plant *Stachys byzantina*.

2. The fibrous structure according to claim 1 wherein the fibrous structure comprises greater than 75% by weight on a dry fiber basis of pulp fibers.

3. The fibrous structure according to claim 1 wherein the fibrous structure comprises greater than 90% by weight on a dry fiber basis of pulp fibers.

4. The fibrous structure according to claim 1 wherein the fibrous structure comprises 100% or less by weight on a dry fiber basis of pulp fibers.

5. The fibrous structure according to claim 1 wherein the pulp fibers comprise tropical hardwood fibers selected from the group consisting of: eucalyptus fibers, acacia fibers, and mixtures thereof.

6. The fibrous structure according to claim 1 wherein the pulp fibers comprise hardwood fibers, and wherein the fibrous structure comprises less than 50% by weight on a dry fiber basis of hardwood fibers.

7. The fibrous structure according to claim 1 wherein fibrous structure is void of hardwood fibers.

8. The fibrous structure according to claim 1 wherein the softwood fibers comprise northern softwood kraft fibers.

9. The fibrous structure according to claim 1 wherein the softwood fibers comprises southern softwood kraft fibers.

10. The fibrous structure according to claim 1 wherein the fibrous structure further comprises one or more synthetic fibers.

11. The fibrous structure according to claim 1 wherein an exterior layer of the fibrous structure comprises one or more of the trichome fibers.

12. The fibrous structure according to claim 1 wherein the fibrous structure comprises a softening agent.

13. The fibrous structure according to claim 12 wherein the softening agent is selected from the group consisting of: quaternary ammonium compounds, silicones, and mixtures thereof.

14. The fibrous structure according to claim 1 wherein the fibrous structure exhibits a basis weight of greater than 21 g/m².

15. A layered fibrous structure exhibiting a basis weight of from about 10 to about 120 g/m², wherein the fibrous structure comprises greater than 50% by weight on a dry fiber basis of pulp fibers comprising trichome fibers, wherein greater than 0% but less than 20% by weight on a dry fiber basis of the pulp fibers are softwood fibers, and wherein the fibrous structure is void of hardwood fibers.

16. The fibrous structure according to claim 15 wherein the fibrous structure comprises greater than 75% by weight on a dry fiber basis of pulp fibers.

17. The fibrous structure according to claim 15 wherein the weight ratio of softwood fibers to non-softwood fibers within the fibrous structure is less than 1:4.

18. A layered fibrous structure exhibiting a basis weight of from about 10 to about 120 g/m², wherein the fibrous structure comprises greater than 50% by weight on a dry fiber basis of pulp fibers comprising trichome fibers, wherein greater than 0% but less than 20% by weight on a dry fiber basis of the pulp fibers are softwood fibers, and wherein the weight ratio of softwood fibers to non-softwood fibers within the fibrous structure is less than 1:4.

19. The fibrous structure according to claim 18 wherein the fibrous structure comprises greater than 75% by weight on a dry fiber basis of pulp fibers.

20. The fibrous structure according to claim 18 wherein the fibrous structure comprises greater than 90% by weight on a dry fiber basis of pulp fibers.

21. The fibrous structure according to claim 18 wherein the fibrous structure comprises 100% or less by weight on a dry fiber basis of pulp fibers.

22. The fibrous structure according to claim 18 wherein one or more of the trichome fibers are derived from a plant in the *Stachys* genus.

23. The fibrous structure according to claim 22 wherein one or more of the trichome fibers are derived from a plant *Stachys byzantina*.

24. The fibrous structure according to claim 18 comprising tropical hardwood fibers selected from the group consisting of: eucalyptus fibers, acacia fibers, and mixtures thereof.

25. The fibrous structure according to claim 18 wherein the pulp fibers comprise hardwood fibers, and wherein the fibrous structure comprises less than 50% by weight on a dry fiber basis of hardwood fibers.

26. The fibrous structure according to claim 18 wherein the fibrous structure is void of hardwood fibers.

27. The fibrous structure according to claim 18 wherein the softwood fibers comprise northern softwood kraft fibers.

28. The fibrous structure according to claim 18 wherein the softwood fibers comprise southern softwood kraft fibers.

29. The fibrous structure according to claim 18 wherein the fibrous structure comprises one or more synthetic fibers.

30. The fibrous structure according to claim 18 wherein the pulp fibers in an exterior layer of the fibrous structure comprise one or more trichome fibers.

31. The fibrous structure according to claim 18 wherein the fibrous structure comprises a softening agent.

32. The fibrous structure according to claim 31 wherein the softening agent is selected from the group consisting of: quaternary ammonium compounds, silicones, and mixtures thereof.

33. The fibrous structure according to claim 18 wherein the fibrous structure exhibits a basis weight of greater than 21 g/m².

* * * * *